United States Patent
Ives

(10) Patent No.: US 6,691,706 B2
(45) Date of Patent: Feb. 17, 2004

(54) PERSONAL HUMIDIFIER

(76) Inventor: Thomas Harrison Ives, 4500 W. Speedway Blvd., Tucson, AZ (US) 85745

(*) Notice: Subject to any disclaimer, the term of this patent is extended or adjusted under 35 U.S.C. 154(b) by 0 days.

(21) Appl. No.: 10/034,445

(22) Filed: Jan. 2, 2002

(65) Prior Publication Data

US 2003/0121518 A1 Jul. 3, 2003

(51) Int. Cl.[7] .................. A61M 15/00; A61M 16/00
(52) U.S. Cl. ..................... 128/204.13; 128/204.11
(58) Field of Search .................. 128/201.13, 201.22, 128/200.28, 202.17, 203.29, 204.11, 204.12, 204.13

(56) References Cited

U.S. PATENT DOCUMENTS

| | | | | |
|---|---|---|---|---|
| 1,056,988 | A | * | 3/1913 | Greene ................ 128/201.22 |
| 2,292,568 | A | * | 8/1942 | Kanter et al. ........ 128/203.28 |
| 3,683,907 | A | * | 8/1972 | Cotabish .............. 128/200.28 |
| 4,150,671 | A | * | 4/1979 | Tiger .................... 128/201.13 |
| 4,196,728 | A | * | 4/1980 | Granite ................ 128/201.13 |
| 4,269,183 | A | * | 5/1981 | Hunt .................... 128/201.13 |
| 4,593,688 | A | * | 6/1986 | Payton ................. 128/200.28 |
| 4,610,247 | A | * | 9/1986 | Stroup ................. 128/201.28 |
| 4,705,033 | A | * | 11/1987 | Halfpenny ........... 128/201.13 |
| 5,007,114 | A | * | 4/1991 | Numano ...................... 2/206 |
| 5,010,594 | A | * | 4/1991 | Suzuki et al. ............... 2/206 |
| 5,595,173 | A | * | 1/1997 | Dodd, Jr. ............ 128/201.13 |
| 5,697,363 | A | * | 12/1997 | Hart .................... 128/201.24 |
| 6,065,473 | A | * | 5/2000 | McCombs et al. .. 128/204.18 |
| 6,247,470 | B1 | * | 6/2001 | Ketchedjian ........ 128/200.28 |
| 6,354,293 | B1 | * | 3/2002 | Madison ............. 128/204.13 |
| 6,450,166 | B1 | * | 9/2002 | McDonald et al. .. 128/206.27 |

* cited by examiner

*Primary Examiner*—Weilun Lo
*Assistant Examiner*—Mital Patel
(74) *Attorney, Agent, or Firm*—Michael Shippey

(57) ABSTRACT

Personal Humidifier with a horseshoe shaped headset made of plastic and being hollow in construction, the headset having an integral centrally located accordion type connection that allows each end of the headset to flex outward to snuggly fit on a user's head, the headset terminating at one end in a flexible tubular member, the tubular member terminating in a wicking material, the wicking material being covered by a removable, replaceable screen cover, the tubular member and the wicking material being supported by a hand bendable metal wire, the metal wire allowing the user to position the tubular member and the wicking material in close proximity to the user's nose, the wicking material penetrating into one end of the hollow headset and traveling the entire length of the headset, the hollow headset capable of retaining water or the like, the water capable of traveling along the wicking material to provide moisture in close proximity to the user's nose, the water retaining headset being refillable by removing a fill cap located at the top of the headset, and the cap having a filter to let air into the hollow headset but not to let water out.

1 Claim, 4 Drawing Sheets

PERSONAL HUMIDIFIER

BACKGROUND OF THE INVENTION

This invention relates generally to the field of humidification devices, and more particularly to a personal humidifier.

Low humidity environments can be problematic to people in that the drying out of the nasal passage can lead to irritation of the nose, lungs and other related health problems. Modern medical professionals suggest that an extremely low humidity environment can even prove fatal to humans. One location that is noted for its low humidity conditions is in the passenger compartment of commercial airplanes. Although there are provisions for moistening the air in an airplane, these moistening devices are sometimes not properly utilized and maintained thereby creating a low humidity environment that is familiar to most airline travelers. This low humidity condition is particularly disturbing to individuals on airplane trips having a travel time of five hours or more.

Various types of humidifiers have been designed and manufactured to help increase the humidity in an otherwise dry environment. These devices tend to be somewhat cumbersome and are usually powered by electricity that powers a steam generator and fan or, more recently, an ultrasonically pulsating electric transducer.

Although current humidifiers do help people to breath moist air, they are not portable, light weight devices and usually require electricity to work. These devices do not lent themselves to be used as personal humidity generating devices in a location such as an airplane.

SUMMARY OF THE INVENTION

The primary object of the invention is to provide a personal humidifier that can be worn by a person while in a low humidity environment.

Another object of the invention is to provide a personal humidifier that can easily adapt to fit an any user's head.

Another object of the invention is to provide a personal humidifier that is compact and light weight.

A further object of the invention is to provide a personal humidifier where the elements that comes in contact with the user's nose is removable and replaceable.

Other objects and advantages of the present invention will become apparent from the following descriptions, taken in connection with the accompanying drawings, wherein, by way of illustration and example, an embodiment of the present invention is disclosed.

Personal Humidifier comprising: a horseshoe shaped headset made of plastic and being hollow in construction, said headset having an integral centrally located accordion type connection that allows each end of the headset to flex outward to snuggly fit on a user's head, said headset terminating at one end in a flexible tubular member, said tubular member terminating in a wicking material, said wicking material being covered by a removable, replaceable screen cover, said tubular member and said wicking material being supported by a hand bendable metal wire, said metal wire allowing the user to position said tubular member and said wicking material in close proximity to the user's nose, said wicking material penetrating into one end of said hollow headset and traveling the entire length of said headset, said hollow headset capable of retaining water or the like, said water capable of traveling along said wicking material to provide moisture in close proximity to the user's nose, said water retaining headset being refillable by removing a fill cap located at the top of said headset, and said cap having a filter means to let air into said hollow headset but not to let water out.

The drawings constitute a part of this specification and include exemplary embodiments to the invention, which may be embodied in various forms. It is to be understood that in some instances various aspects of the invention may be shown exaggerated or enlarged to facilitate an understanding of the invention.

GENERAL DESCRIPTION OF THE DRAWINGS

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
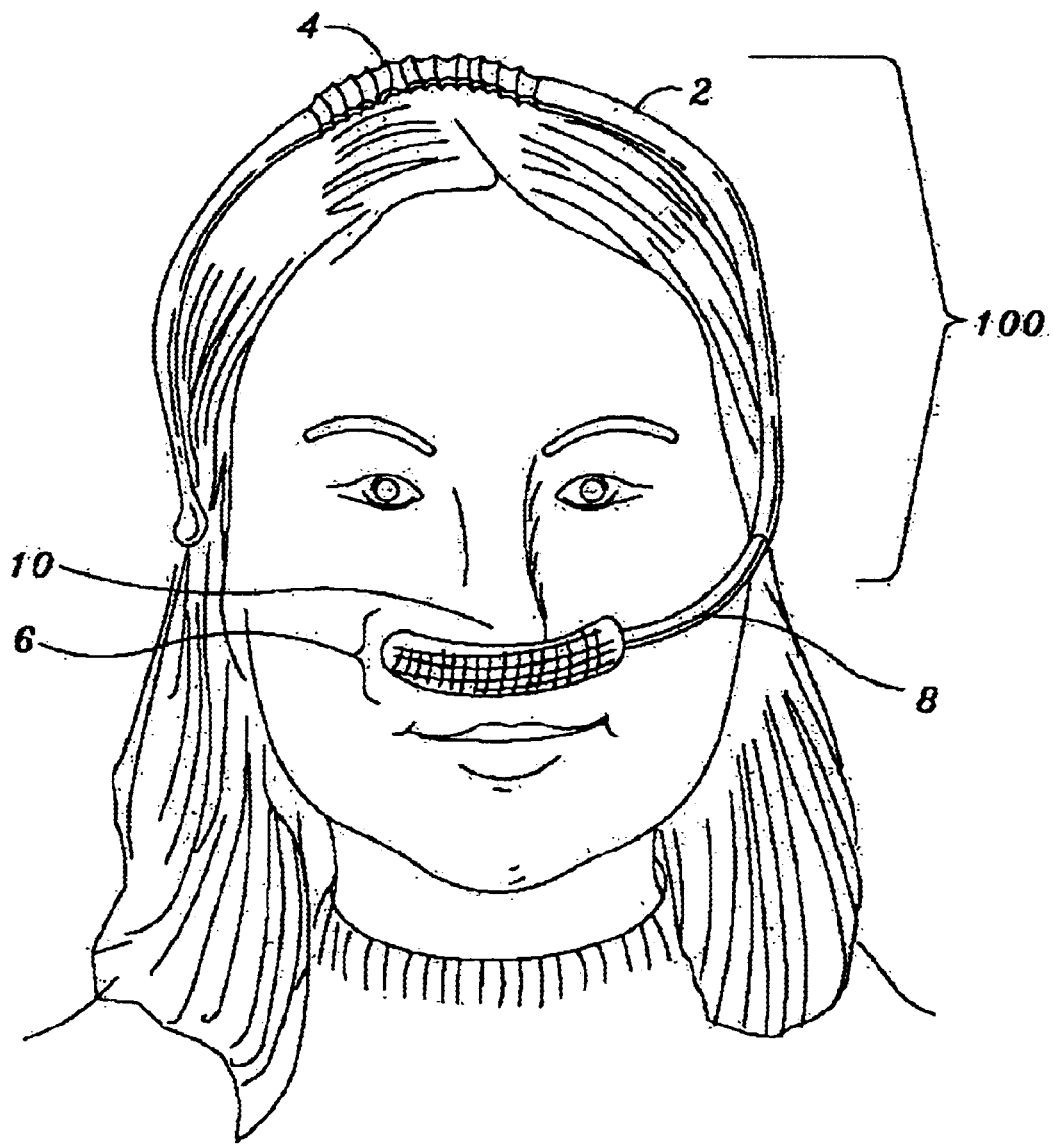
FIG. 1 is a perspective front view of a person wearing the personal humidifier of the present invention.
Figure 2:
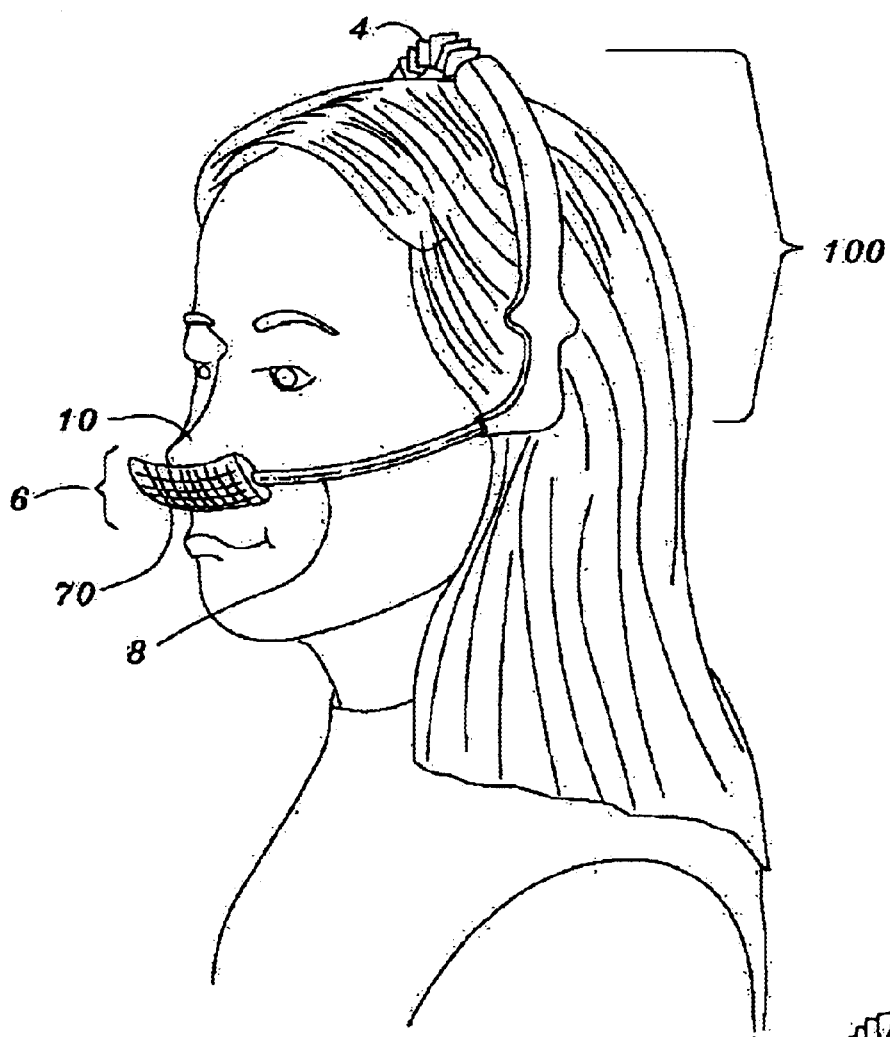
FIG. 2 is a perspective side view of a person wearing the personal humidifier of the present invention.
Figure 3:
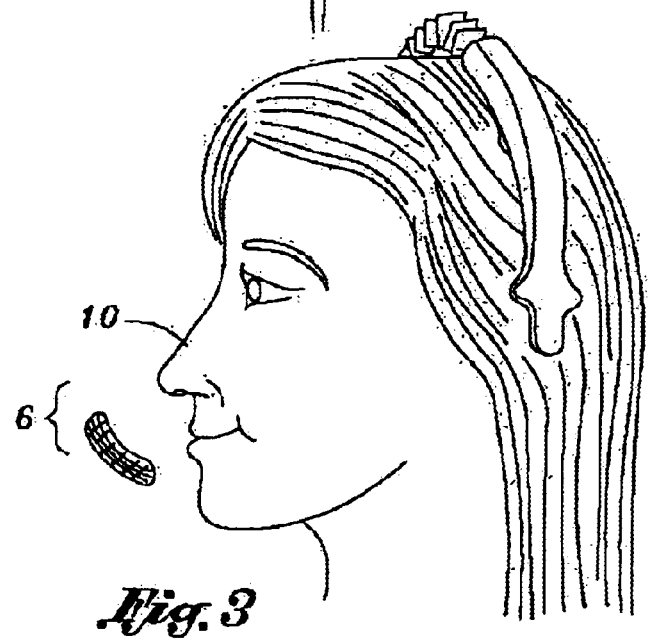
FIG. 3 is a side view showing the proximity of the wick assembly to the user's nose.
Figure 4:
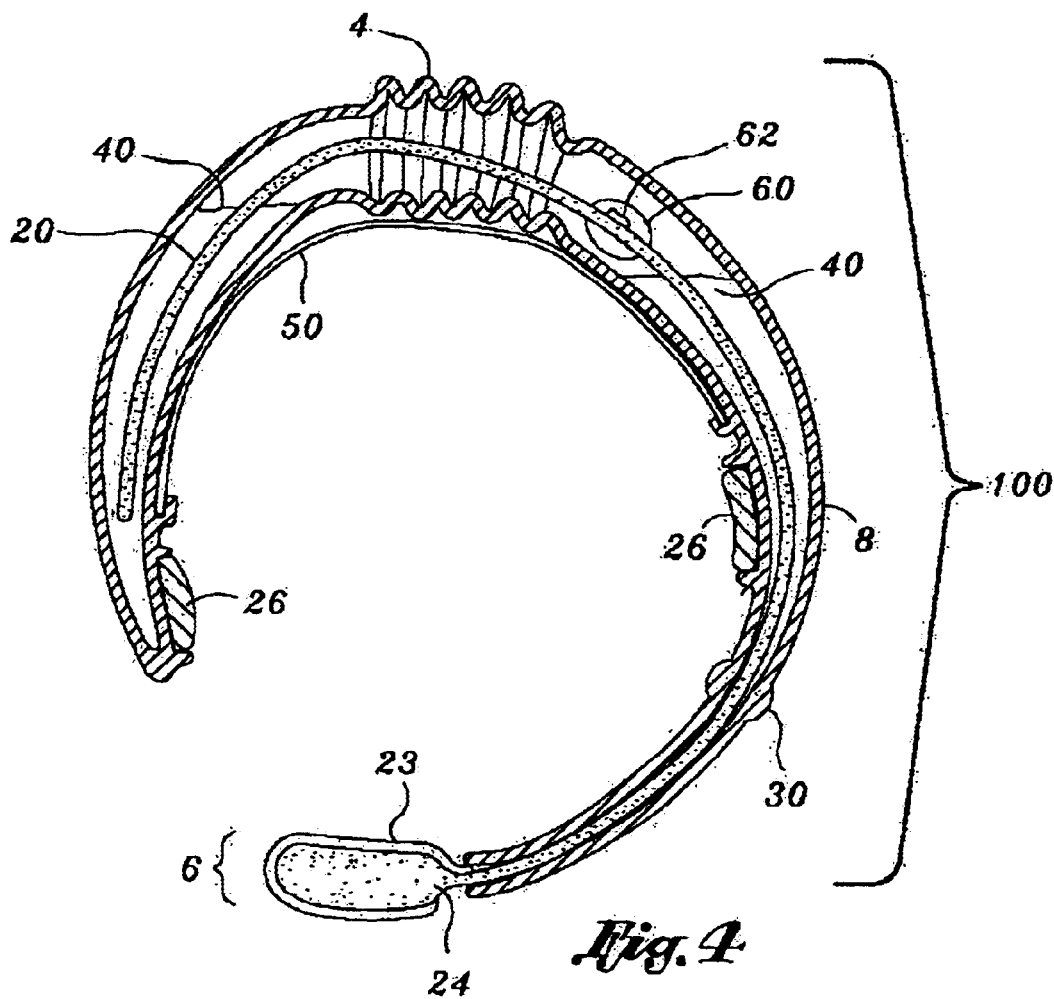
FIG. 4 is a section view showing the inside of the present invention.
Figure 5:
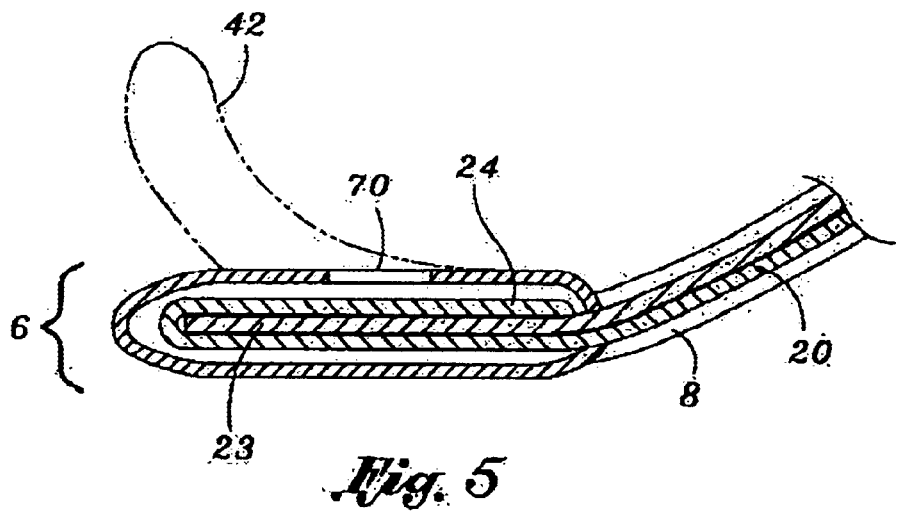
FIG. 5 is a side section view of the wick assembly.
Figure 6:
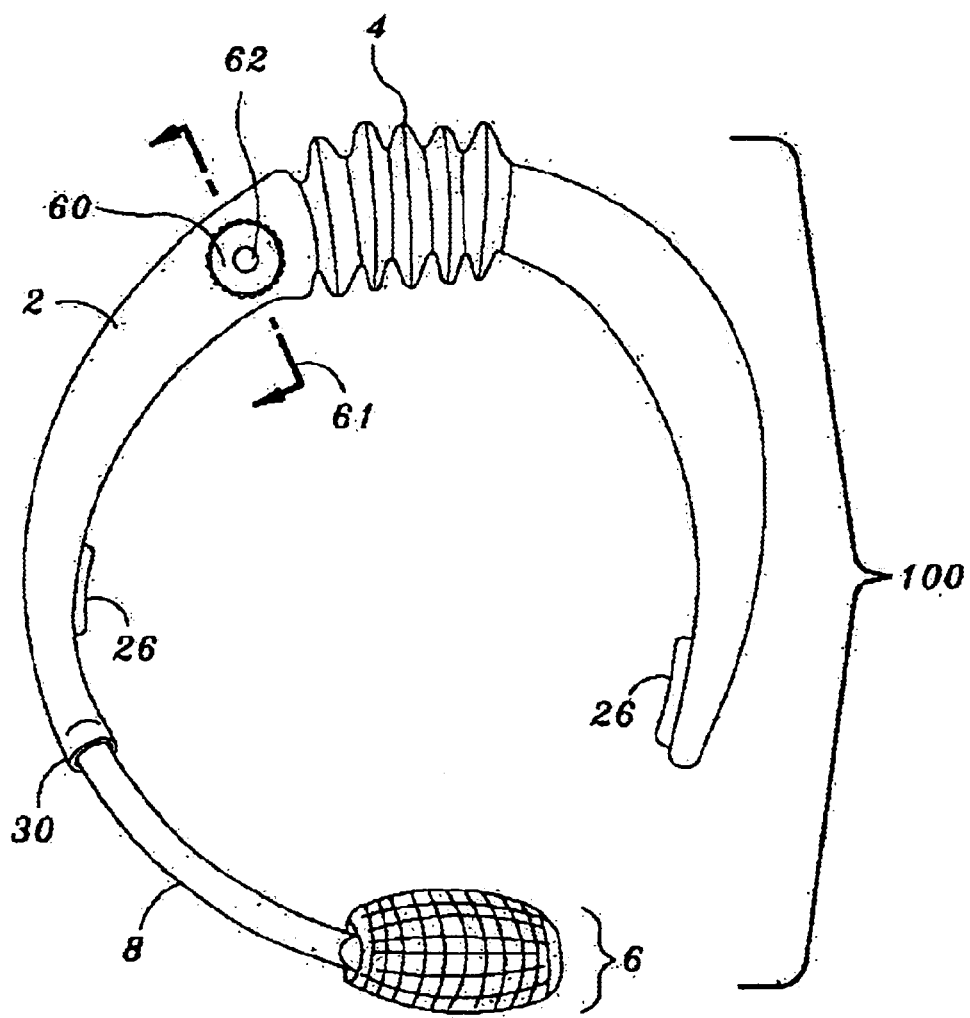
FIG. 6 is a rear view of the present invention.
Figure 7:
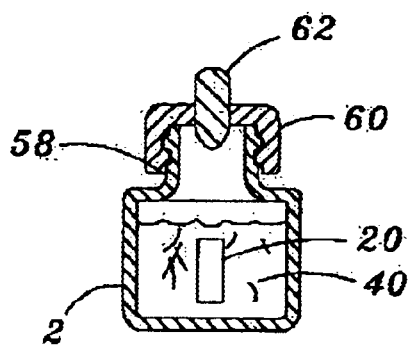
FIG. 7 is a section view of the fill cap.

Referring now to FIGS. 1 and 2 we see a person wearing the personal humidifier 100 of the present invention. A hollow, water retaining, horseshoe shaped headset member 2 is molded from rigid plastic and is affixed the the users head in much the same way that a standard telephone headset may fit. A centrally located accordion shaped portion 4 creates a flexible spring biased joint that helps the headset fit snuggly on the user's head. One end of the headset 2 terminates in a flexible tube 8 that in turn terminates in a wick assembly 6. FIG. 3 shows the proximity of the wicking assembly 6 to the user's nose 10. As can be seen, the wicking assembly is in close proximity to, but not touching, the user's nose 10. In this configuration the user can have access to the moisture contained within the wick thereby increasing the humidity factor of the air breathed in through the nose of the user. FIG. 4 shows a section view of the entire assembly 100 of the present invention. In this view, we can clearly see the hollow nature of headset 2 and the water enclosed 40 within the headset. A wicking material 20 traverses the entire length of the interior of the headset assembly 2 so that water contained within the headset assembly 2 can be drawn out of the headset through tube holding joint 30 and into a flexible tube 8 and finally terminating in a wider wick portion 24 that can be positioned under the user's nose. A bendable wire made of copper or stainless steal or the like, travels inside tube 8 along with wick 20 and terminates by wrapping 23 around the perimeter of wick portion 24. Resilient head gripping members 26, 28 help hold the present invention 100 to the user's head. Fill cap 60 and breather filter 62 can be partially seen and are more clearly illustrated in FIGS. 6 and 7. An optional horseshoe shaped metal spring member 50, standard in most telephone headsets, is shown in case the natural spring quality of the accordion section 4 is not sufficient to hold the headset 2 firmly on the user's head. FIG. 5 shows a side section view of the wick assembly 6. Wick material 20 folds over wire support 23. Wire support 22 and 23 are bendable so that the wick assembly 6 can be positioned near the user's nose and so that the assembly 6 can be bent into a concave shape as shown by dotted line 42 thereby conforming more closely to the underside of the user's nose. Removable and replaceable cover 70 is constructed of flexible plastic screen material that lets the user have access to the moisture contained in the wick 24 but does not allow the user's nose to become moist due to contact with the wick 24. FIG. 6 shows a rear view of the present invention 100. In this view one can clearly see the fill cap 60 and a breather filter 62 that allows air in but does not allow water out. This configuration means that a vacuum is not allowed to build up within the hollow headset assembly 2. Section line 61 defines the view shown in FIG. 7 which clearly shows fill cap 60 and its relation to threaded shoulder 58 that rises from and is integral to headset 2. Water 40 and wick 20 can also be clearly seen.

The above descriptions and illustrations show that the present invention is an effective means for providing additional moisture to a person while in an otherwise dry environment such as in the cabin of an airplane. The present invention requires no electricity, is light weight and is inexpensive to manufacture.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Personal Humidifier comprising: a horseshoe shaped headset made of plastic and being hollow in construction; said headset having an integral centrally located accordion connection that allows each end of the headset to flex outward to snuggly fit on a user's head; said headset terminating at one end in a flexible tubular member; said tubular member terminating in a wicking material; said wicking material being covered by a removable, replaceable screen cover; said tubular member and said wicking material being supported by a hand bendable metal wire; said metal wire adapted to allow the user to position said tubular member and said wicking material in close proximity to the user's nose; said wicking material penetrating into one end of said headset and traveling an entire length of said headset; said headset capable of retaining water; said water capable of traveling along said wicking material to provide moisture in close proximity to the user's nose; said headset being refillable by removing a fill cap located atop of said headset; and said cap having a filter means to let air into said headset but not to let water out.

* * * * *